United States Patent
Nguyen

(10) Patent No.: US 10,166,405 B2
(45) Date of Patent: Jan. 1, 2019

(54) IMAGE-GUIDED RADIOTHERAPY FOR INTERNAL TUMOR BOOST

(71) Applicant: Nam Nguyen, Washington, DC (US)

(72) Inventor: Nam Nguyen, Washington, DC (US)

(*) Notice: Subject to any disclaimer, the term of this patent is extended or adjusted under 35 U.S.C. 154(b) by 620 days.

(21) Appl. No.: 14/745,188

(22) Filed: Jun. 19, 2015

(65) Prior Publication Data
US 2016/0051841 A1    Feb. 25, 2016

Related U.S. Application Data

(63) Continuation-in-part of application No. 14/436,394, filed as application No. PCT/US2013/065283 on Oct. 16, 2013, which is a continuation-in-part of application No. 13/652,821, filed on Oct. 16, 2012, now abandoned.

(51) Int. Cl.
*A61N 5/10*    (2006.01)

(52) U.S. Cl.
CPC ......... *A61N 5/1031* (2013.01); *A61N 5/1042* (2013.01); *A61N 5/1064* (2013.01)

(58) Field of Classification Search
CPC .. A61N 5/1031; A61N 5/1037; A61N 5/1039; A61N 5/1042; A61N 5/1045; A61N 5/1047; A61N 5/1069; A61N 5/107; A61N 5/1071
See application file for complete search history.

(56) References Cited

U.S. PATENT DOCUMENTS

| | | | |
|---|---|---|---|
| 7,606,405 B2 | 10/2009 | Sawyer et al. | |
| 8,173,983 B1 | 5/2012 | Sahadevan | |
| 8,238,520 B2 | 8/2012 | Nord et al. | |
| 2005/0041843 A1 | 2/2005 | Sawyer | |
| 2006/0067469 A1 | 3/2006 | Dooley et al. | |
| 2007/0014454 A1 | 1/2007 | Sawyer et al. | |
| 2009/0130098 A1* | 5/2009 | Goodman | A61K 31/4188 424/133.1 |
| 2010/0228116 A1* | 9/2010 | Lu | A61N 5/103 600/411 |
| 2010/0322381 A1 | 12/2010 | Stahl et al. | |

(Continued)

OTHER PUBLICATIONS

Wu et al. "Simultaneous Integrated Boost Intensity-Modulated Radiotherapy for Locally Advanced Head-and-Neck Squamous Cell Carcinomas. I: Dosimetric Results." International Journal of Radiation Oncology Biology Physics. vol. 56, No. 2, 2003, p. 573-585.*

(Continued)

*Primary Examiner* — Carrie R Dorna

(57) ABSTRACT

A method of image-guided radiotherapy for treatment of a radio-resistant or radio-sensitive tumor. A three-dimensional visualized tumor image is obtained and the boundary of the tumor is identified. A boosted radiation dose of treatment is designated and applied to a boost region within the tumor boundary. A predetermined prescribed radiation dose is simultaneously applied with the boosted radiation dose within the tumor boundary and in a planning target volume region, which is outside of the tumor boundary. The boosted radiation dose outside of the boost region decreases at a boost dose decreasing rate such that the boosted radiation dose is equal to the predetermined prescribed radiation dose at the tumor boundary.

1 Claim, 7 Drawing Sheets

(56) References Cited

U.S. PATENT DOCUMENTS

2011/0075806 A1 3/2011 Nord et al.
2012/0326057 A1 12/2012 Remeijer et al.

OTHER PUBLICATIONS

Teh et al. "The treatment of primary and metastatic renal cell carcinoma (RCC) with image-guided stereotactic body radiation therapy (SBRT)." Biomedical Imaging and Intervention Journal. vol. 3, No. 1, 2007.*
Sause, WT et al.; Fraction size in external beam radiation therapy in the treatment of melanoma; Int J Radiat Oncol Biol Phys; Mar. 1991; 20(3):429-32 (Abstract).
Radiation Therapy Oncology Group, RTOG 0920, A Phase III Study of Postoperative Radiation Therapy (IMRT) +/− Cetuximab for Locally Advanced Resected Head and Neck Cancer, Dec. 6, 2010.
Nancy Lee, M.D, Adam Garden, M.D., Alan Kramer, M.D, Ping Xia, Ph.D., Radiation Therapy Oncology Group, RTOG 0225: A Phase II Study of Intensity Modulated Radiation Therapy (IMRT) +/− Chemotherapy for Nasopharyngeal Cancer, May 26, 2005.
Schofield, Debbie et al., Review and guidelines for treating head and neck tumors using IMRAT and VMAT, AAPM 2010.
Schofield, Debbie; Farber, Dana, "The Use of IMRT in the Treatment of Head and Neck Cancer"; 2012.
Mayo, Charles; "Review and guidelines for treating head and neck tumors using IMRT and VMAT"; 2012.

* cited by examiner

IMAGE-GUIDED RADIOTHERAPY FOR INTERNAL TUMOR BOOST

CROSS REFERENCE

This application is a continuation-in-part and claims the benefit of U.S. patent application Ser. No. 14/436,394 filed on Apr. 16, 2015, which is a 371 of PCT/US13/65283 filed on Oct. 16, 2013, which is a continuation-in-part and claims the benefit of U.S. patent application Ser. No. 13/652,821 filed on Oct. 16, 2012, the specification(s) of which is/are incorporated herein in their entirety by reference.

FIELD OF THE INVENTION

The present invention relates to image-guided radiotherapy, and more particularly, to image-guided radiotherapy for tumor treatment.

BACKGROUND OF THE INVENTION

Radiotherapy is a proven modality for cancer cure similar to surgery for tumors of all sites. The probability to destroy the cancer locally is proportional to the radiation dose delivered to the cancer sites. Most often, the effectiveness of radiotherapy is limited by the radiation dose that can safely be delivered to the normal organs adjacent to the tumor.

Serious complications may occur if the normal organs receive a radiation dose that exceeds their tolerance to radiation. Paralysis (spinal cord injury), blindness (optic nerve injury), stroke (brain injury), bleeding (blood vessels injury), inflammation of lungs (lungs injury) and bowels (bowels injury) may lead to death or seriously affect patient quality of life are well known complications of radiation treatment. Current methods of radiation treatments set a maximum limit for the radiation dose.

For example, in Section 6.4.2.4 Radiation Therapy Oncology Group (RTOG) study number 0225: A Phase II Study of Intensity Modulated Radiation Therapy (IMRT)+/Chemotherapy for Nasopharyngeal Cancer, it is specified that "No more than 20% of any PTV70 (the gross tumor volume with a 5 mm margin) will receive ≥110% of the prescribed dose." The rule limits the toxicity of the treatment to avoid complications.

Referring to FIG. 1B, Tabular Data 1 shows schematic representation of "volumes" in radiation therapy in terms of Gross Target Volume, Clinical Target Volume, Planning Target Volume from Page 5, Chapter 1: The Discipline of Radiation Oncology, Book: Perez and Brady's Principles and Practice of Radiation Oncology, 5th Edition, published by Lippincott Williams & Wilkins with ISBN-10: 078176369X. This figure clearly shows that the planning target volume (PTV) is beyond the tumor boundary.

Tabular Data 2 shows the Memorial Sloan-Kettering Cancer Center (MSKCC) Clinical Dose Limits and Inverse Planning Algorithm Constraints for Primary Nasopharynx Tumors, excerpted from book "A practical guide to intensity-modulated radiation therapy" (Medical Physics Pub., 2003, ISBN: 1930524137), Chapter 10: IMRT for head and neck Cancer, Table 10.3, page 201. The table clearly regulates that the maximum dose is 105%.

TABULAR DATA 2

| | | Inverse Plaanning Algorithm Constraint Template | | | |
|---|---|---|---|---|---|
| Structure | Clinical Dose Limits | Presription Dose (%) | Maximum Dose (%)/ Penalty | Minimum Dose (%)/ Penalty | Dose (%)-% Volume Constraint/Penalty |
| $PTV_{el}$ | $D_{95} \geq 50$ Gy (95% of 54 Gy) Max. Dose ≤64.8 Gy (120% of 54 Gy) | 54 Gy (77%) | 56.7 Gy (81 %)/50 | 51.3 Gy (73%)/50 | NA |
| $PTV_{gr}$ | $D_{95} \geq 70$ Gy (100% of 70 Gy) Max. Dose ≤84 Gy (120% of 70 Gy) | 70 Gy (100%) | 66.5 Gy (105%)/50 | 73.5 Gy (95%)/50 | NA |
| Spinal Cord | Max. Dose ≤45 Gy | | 28 Gy (40%)/50 | | NA |
| Brainstem | Max. Dose ≤50 Gy | | 35 Gy (50%)/50 | | NA |
| Parotid Gland | Mean Dose ≤26 Gy | | 68 Gy (98%)/50 | | ≥ 21 Gy (30%) to ≤30% Volume/50 |
| Cochlea | Max. Dose ≤60 Gy | | 56 Gy (80%)/50 | | NA |

Tabular Data 3 shows the compliance criteria of radiation treatment in Radiation Therapy Oncology Group (RTOG) study number 0920: A Phase III Study of Postoperative Radiation Therapy (IMRT)+/−Cetuximab for Locally-Advanced Resected Head and Neck Cancer, section 6.7, page 27. The criteria lists in Row 1 that any Radiation dose (RT)>66Gy as a major variation should be avoided at any rate. The 66Gy corresponds to a 10% increase over PTV 60Gy.

TABULAR DATA 3

|  | Per Protocol | Minor Variation | Major Variation |
|---|---|---|---|
| Total RT dose to PTV60 (to 95% of PTV60) | 60-64 Gy | 58-60 or 64-66 Gy | <58 or >66 Gy |
| Minimum dose ("cold spot" within PTV60, not including portion of PTV near (<8 mm) skin) | 56-60 Gy | 54-56 Gy | >54 Gy |
| Maximum dose ("hot spot") within PTV60* | <70 Gy | 70-72 Gy | >72 Gy |
| Maximum dose ("hot spot" outside of PTV60) | <66 Gy | 66-70 Gy | >70 Gy |
| Definition of CTV60 | Base on case review by study chair. | | |
| Definition of PTV60 | Base on case review by study chair. | | |
| Total RT dose to spinal cord PRV (0.03 cc) | <48 Gy | 48-50 Gy | >50 Gy |
| Total RT dose to spinal cord PRV (0.01 cc) | <50 Gy | 50-52 Gy | >52 Gy |
| Definition of Spinal cord PRV | Base on case review by study chair. | | |
| Overall RT treatment time | | | >50 days (without a medically appropriate indication for delay) |
| Non-Medically Indicated Treatment Interruptions | 0-2 | 2-4 | >4 |

*Not including the region of PTV60 that falls within PTV66 (if applicable)

Tabular Data 4 shows the Critical Normal Structures in Radiation Therapy ONCOLOGY Group (RTOG) study number 0225: A Phase II Study of Intensity Modulated Radiation Therapy (IMRT)+/Chemotherapy for Nasopharyngeal Cancer, section 6.4.3 Critical Normal Structures, page 7. The Critical Normal Structures discloses clearly that 60 Gy or 1% of the PTV cannot exceed 65 Gy (which is close to 10% increase over PTV 60Gy radiation.)

TABULAR DATA 4

6.4.3 Critical Normal Structures
DVH's must be generated for all critical normal structures and the unspecified tissues. Dose constraints to normal tissues will be as follows:

| Brainstem, optic nerves, chiasm | 54 Gy or 1% of the PTV cannot exceed 60 Gy |
|---|---|
| Spinal Chord | 45 Gy or 1 cc (if 1% is used, depends on length of the cord outlined) of the PTV cannot exceed 50 Gy |
| Mandible and T-M joint | 70 Gy or 1 cc of the PTV cannot exceed 75 Gy |
| Temporal lobes | 60 Gy or 1% of the PTV cannot exceed 65 Gy |

Unspecified tissue outside the targets: ≤100% of the dose prescribed to PTV$_{70}$. No more than 5% of the non-target tissue can receive greater than 70 Gy. Participants are strongly encourages to remain within these limits.

Tabular Data 5 shows the hotspot radiation regulation in a presentation (slide 13) of a research taken at Dana-Farber/Brigham & Women's Cancer Center and Harvard Medical School ("Variability in planning criteria and plan evaluation", Laurence Court, the American Association of Physicists in Medicine annual meeting 2010). The slide clearly shows the aiming for hotspots radiation is limited to <110% of the radiation dose.

Tabular Data 5

| Hotspots |
|---|
| 105%+ |
| DFCI: Aim for 5%, <110% |
| UMass: aim for <110%. Typically 8% vol < 10% (will accept ~10% of PTV > 110% if necessary) |
| 105-110% (MDACC) |
| MGH: 110-115%, 120%+ if necessary |
| Impact of chemotherapy |
| AAPM 2010                                    13 |

However, the use of a low radiation dose can be ineffective for curing cancer cure and a patient can die from uncontrolled tumor growth or from complications resulting from tumor destruction of the normal organs. Thus, the clinician is often faced with a dilemma: either let the cancer kill the patient or expose the patient to serious injury from radiation complications. Therefore, there is a need for a balanced method for image-guided radiotherapy for providing higher dose for tumor tissues while avoiding excessive radiation to normal tissues. The present invention features a boost dose of radiation with no upper limit and that is applied to both high and low tumor concentrations.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

In one embodiment of this application, the subject disclosure features an image-guided radiotherapy method for treating a tumor having radio-sensitive or radio-resistant cells. In some embodiments, the method comprises obtaining a three-dimensional visualized tumor image to identify the tumor, identifying a tumor boundary of the tumor, identifying a planning target volume (PTV) region outside of the tumor boundary, identifying a boost region within the tumor boundary, identifying a neighboring structure adjacent to the tumor, applying a boosted radiation dose in the boost region, simultaneously applying with the boosted radiation dose a predetermined prescribed radiation dose in the PTV region and within the tumor boundary, and repeating steps a. through g. for each subsequent treatment.

The present invention has at least the following advantageous features and that are not taught or suggested by the prior art:
1. The method allows for treatment of radiation-resistant or radiation-sensitive tumors.
2. There is no upper limit to the boosted radiation dose. The boosted radiation dose is at least % 110 of the prescribed radiation dose.

Prior to this present invention, none of the prior art references teach or suggest the features of the present invention. For example, U.S. Publication No. 2007/0014454 by Sawyer only allows for higher radiation doses if regions of the tumor are radiation-resistant. The present invention applies the boosted radiation dose to any tumor regardless of its radio-resistivity or radio-sensitivity.

As another example, U.S. Publication No. 2006/0067469 by Dooley defines an inverse or forward planning method with a dose limit for the tumor and acceptable dose ranges for predetermined regions, i.e. the upper and lower limit of radiation for delivering the requisite doses of radiation to the tumor. The present invention requires no upper limit of radiation for the boosted radiation dose at the boost region.

Moreover, U.S. Publication No. 2011/0075806 by Nord uses the homogeneity index (HI) and conformity index (CI) to optimize the tumor treatment plan. HI and CI specify that HI >2.5 and CI >2.5 would constitute a major deviation of the treatment plan, i.e. excessive dose to the tumor is not allowed. The present invention allows for excessive dosing, i.e. the boosted radiation dose, at the boost region.

BRIEF DESCRIPTION OF THE DRAWINGS

In FIG. 1A, a tumor (110) has a tumor boundary (115) enclosed by the gross tumor boundary. Clinical tumor volume is enclosed by GTV boundary (116) and planning tumor volume is enclosed by PTV boundary (118).

(FIG. 1B is modified from Perez C A, Purdy JA. Rationale for treatment planning in radiation therapy. In: Levitt S H, Khan F M, Potish R A, eds. *Levitt and Tapley's technological basis of radiation therapy: practical clinical applications*, 2nd ed. Philadelphia: Lea & Febiger, 1992; with permission.)

FIG. 6a shows the present method and FIG. 6b shows the traditional method. In FIG. 6a, the radiation dose decreasing curve results from the boosted radiation dose treatment applied at the boost region, more specifically, the decrease of the boosted radiation dose from the boost region to the tumor boundary. As shown in the boosted radiation dose decreasing curve, the boosted radiation dose inside the tumor boundary is significantly higher as compared to the prescribed dose of FIG. 6b. However, the boosted radiation dose decrease at the tumor boundary and outside of the tumor boundary is the same as the conventional treatment. The boosted radiation dose is escalated within the tumor and there are no limitations to the boosted radiation dose that can be delivered inside the boosted region. FIG. 6 shows that the prescribed radiation dose is applied to the tumor and outside of the tumor within the PTV.

DESCRIPTION OF PREFERRED EMBODIMENTS

Figure 1A:
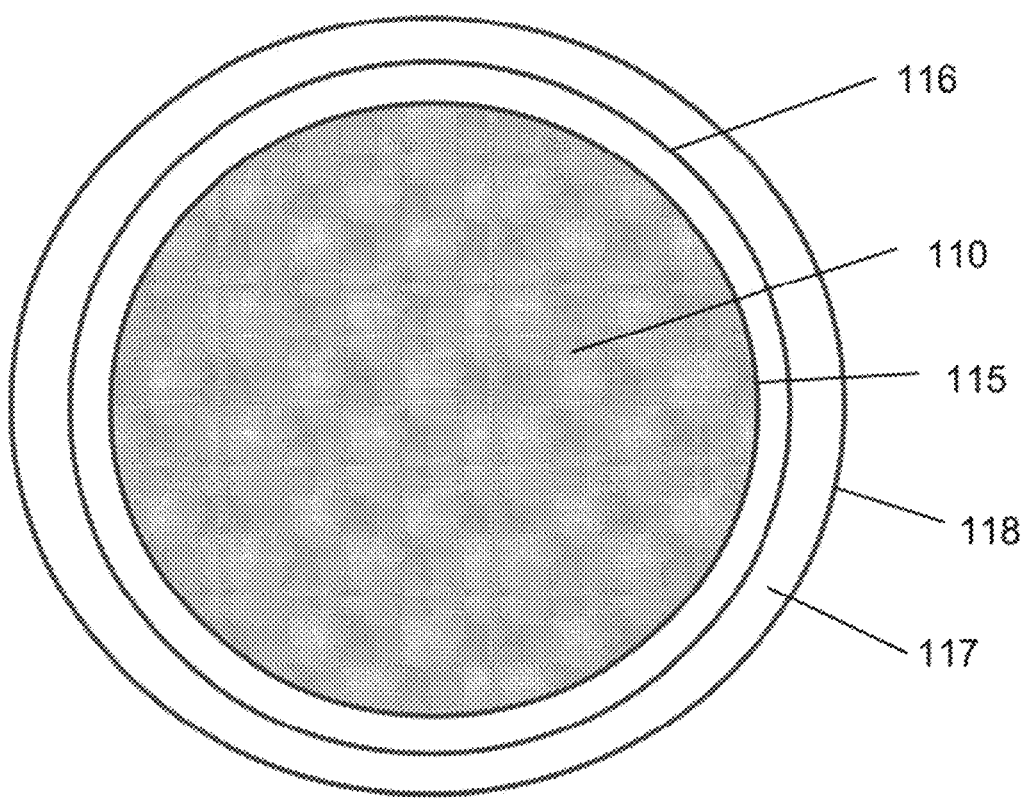
FIG. 1A shows a schematic view for a gross tumor volume (GTV), a clinical tumor volume (CTV) and planning target volume (PTV), wherein the planning target volume (PTV) is the traditional radiation treatment volume and is beyond the tumor boundary.
Figure 1B:
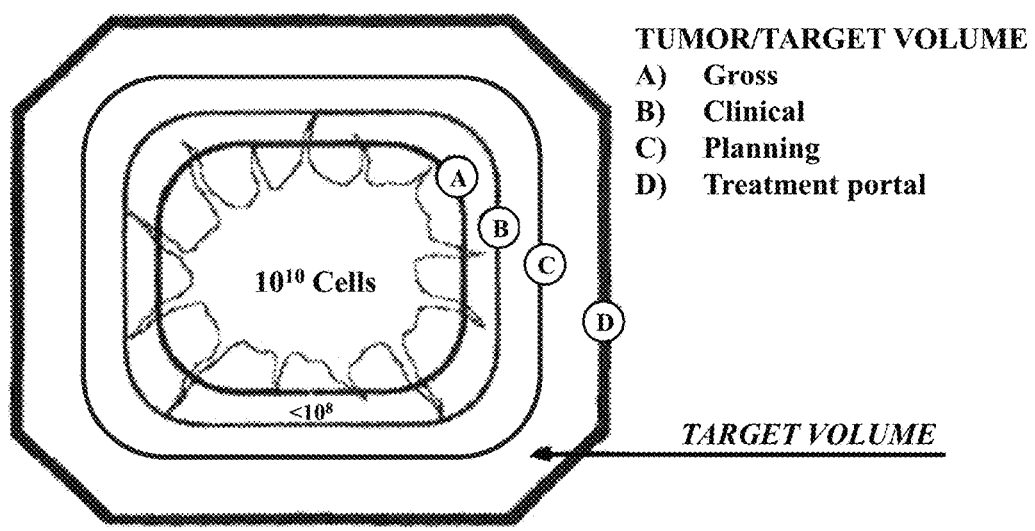
FIG. 1B shows a schematic representation of "volumes" in radiation therapy in terms of Gross Target Volume, Clinical Target Volume, Planning Target Volume. The treatment portal volume includes the tumor volume, potential areas of local and regional microscopic disease around the tumor, and a margin of surrounding normal tissue.
Figure 2:
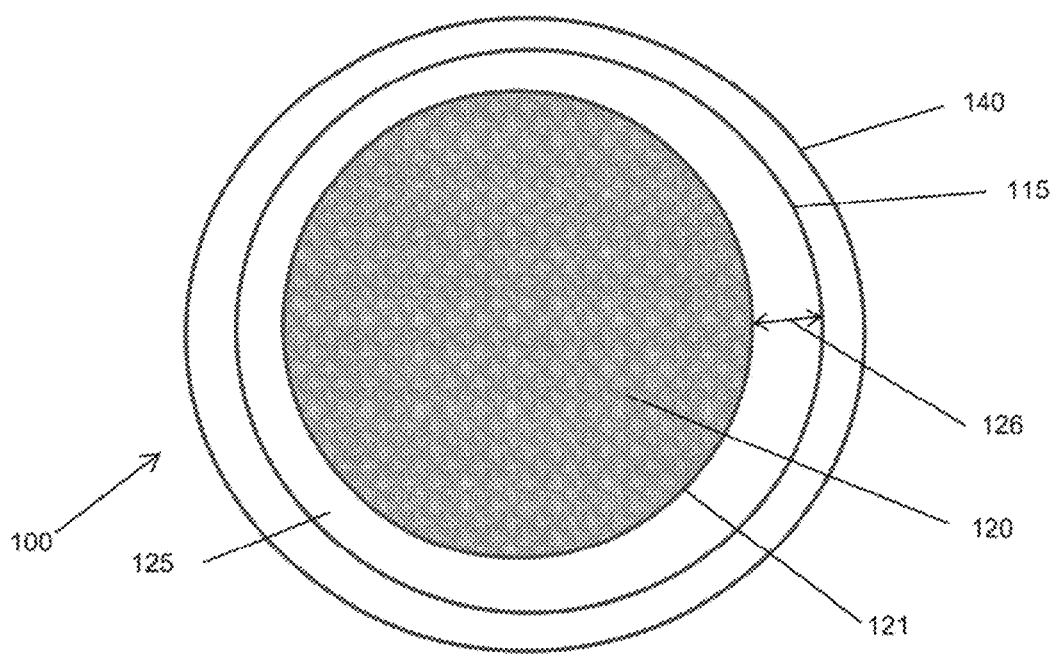
FIG. 2 shows a brief view of a tumor boundary and boosted treatment region of the present invention.
Figure 3:
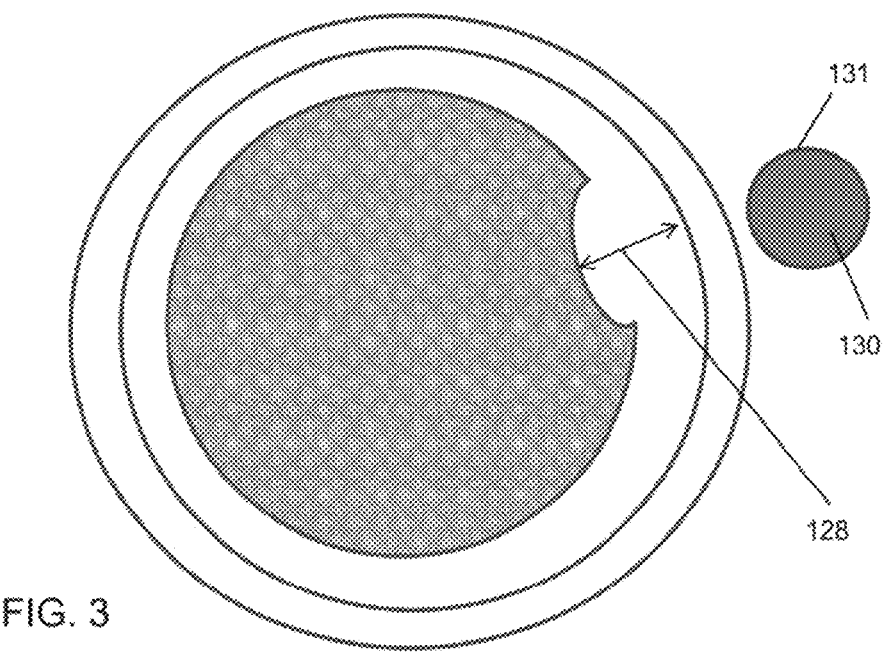
FIG. 3 shows a brief view of a tumor boundary and boosted treatment region when a radiation sensitive normal organ is near the tumor boundary of the present invention.

As used herein, the terms "prescribed radiation dose" or "prescribed dose" means the conventional dose established in the literature for cancer cure. The prescribed dose may be determined from external beam radiotherapy alone or radiotherapy combined with chemotherapy for locally advanced head and neck cancer. As non-limiting examples, the "prescribed dose" for Oropharyngeal cancer, Oral cavity cancer, Laryngeal cancer, Hypopharyngeal cancer is about 7000 cGy, at about 200 cGy per day.

As used herein, the terms "boosted radiation dose" or "boosted dose" is defined as a dose that is at least 110% higher than the prescribed dose.

Referring now to FIG. 1-7, the present invention features an image-guided radiotherapy method for treating a tumor (110) having radio-sensitive or radio-resistant cells. In some embodiments, the method comprises obtaining a three-dimensional visualized tumor image (100) to identify the tumor (110), identifying a tumor boundary (115) of the tumor (110), identifying a planning target volume (PTV) region (117) outside of the tumor boundary (115), identifying a boost region (120) within the tumor boundary (115), identifying a neighboring structure (130) adjacent to the tumor (110), applying a boosted radiation dose in the boost region (120), simultaneously applying with the boosted radiation dose a predetermined prescribed radiation dose in the PTV region (117) and within the tumor boundary (115), and repeating steps a. through g. for each subsequent treatment.

In some embodiments, a predetermined safety region (125) is between the boosted region (120) and the tumor boundary (115). The predetermined safety region (125) can have a predetermined minimum distance (126) from a boosted region boundary (121) to the tumor boundary (115). In other embodiments, the PTV region (117) is between the tumor boundary (115) and a planning target volume boundary (118).

In some embodiments, the neighboring structure (130) is bounded within a neighboring structure boundary (131). The neighboring structure (130) may be a radiation sensitive normal organ near the tumor boundary (115). In other embodiments, the method may further comprise increasing a distance (128) between the tumor (110) and the neighboring structure (130) to avoid excessive radiation influence on the radiation sensitive normal organ. In some embodiments, the predetermined minimum distance is dependent on the importance level and radiation sensitivity level of the normal organ.

In preferred embodiments, the boosted radiation dose outside of the boost region (120) decreases at a boost dose decreasing rate such that the boosted radiation dose at the tumor boundary (115) is equal to the predetermined prescribed radiation dose. In other preferred embodiments, the boosted radiation dose and the predetermined prescribed radiation dose decreases at an average decreasing rate such that the boosted radiation dose and the predetermined prescribed radiation dose at the neighboring structure boundary (131) is below a radiation dose threshold of the neighboring structure (130).

The prescribed radiation dose may be applied simultaneously with the boosted radiation dose. The prescribed radiation dose is applied within the PTV boundary, i.e. outside of the tumor boundary, in order to treat the whole tumor and not miss any portions of the tumor. The predetermined prescribed radiation dose is usually lower than the boosted radiation dose.

Higher boost radiation doses in the boosted region can surpass conventional limits of radiation doses, for example, surpassing by at least 110% or greater. The higher radiation from the boost dose is constrained within the tumor boundary. The higher boost radiation doses can kill the tumor cells more quickly and without negatively affecting the neighboring organs since it decreases to a level below the radiation threshold of the neighboring organs.

In some embodiments, the boosted radiation dose is at least 110% of a predetermined prescribed radiation dose for the tumor. In other embodiments, the boosted radiation dose is at least 120% of a predetermined prescribed radiation dose for the tumor. In still other embodiments, the boosted radiation dose is at least 130% to 150% of a predetermined prescribed radiation dose for the tumor.

In some embodiments, the boosted radiation dose can be applied to all tumors, regardless of their sensitivity to the radiation, for removing more of the tumor mass with each boosted radiation dose. The tumor within the boost region (120) may be either radio-sensitive or radio-resistant.

To verify treatment accuracy, the tumor must be re-imaged before applying each subsequent radiation treatment in order to obtain a new tumor location and size. In an exemplary embodiment, steps a through g is applied for a first radiation treatment of a tumor. The tumor reduces in a size as a result of the first treatment. A second and subsequent radiation treatment is applied to the smaller tumor by repeating steps a through g. A third radiation is applied to the tumor that is further reduced in size by the application of the second radiation treatment. The method is repeated until the tumor is completely eliminated.

In one embodiment, the prescribed radiation dose can range from about 180 to 200 centiGray per day and the boosted radiation dose can range from about 220 to 350 centiGray per day for a tumor that is Squamous Carcinoma, Adeno Carcinoma, Small Cell Carcinoma, Lymphoma Carcinoma or Transitional Cell Carcinoma. In another embodiment, the prescribed radiation dose is about 250 centiGray per day and the boosted radiation dose can range from about 300 to 450 centiGray per day for a tumor that is that is melanoma or renal cancer.

In some embodiments, the average decreasing rate is about 10% per millimeter, i.e. the radiation dose beyond the tumor boundary and within the radiation boundary decreases at an average rate of about 10% per millimeter. For example, the radiation dose beyond the tumor boundary may decrease at a faster rate, such as 15% per millimeter, whereas the radiation dose near the radiation boundary may decrease at a slower rate, such as 5% per millimeter. In other embodiments, the average decreasing rate may be about 15% per millimeter or about 20% per millimeter.

In some embodiments, the tumor is a radiation-sensitive tumor, such as Squamous Carcinoma, Adeno Carcinoma, small cell Carcinoma, Lymphoma Carcinoma or Transitional cell Carcinoma. In some embodiments, the featured image-guided radiotherapy method for tumor treatment is applicable to treatment of neck node less than 3 centimeter (cm) in diameter. In some embodiments, the featured image-guided radiotherapy method for tumor treatment is applicable to treatment of neck nodes with diameter between 3 cm and 6 cm. In some embodiments, the featured image-guided radiotherapy method for tumor treatment is applicable for effective treatment of neck nodes larger than 6 centimeter (cm) in diameter. In some embodiments, the featured image-guided radiotherapy method for tumor treatment is applicable to treatment of locally advanced head and neck cancer that have not spread to distant organs.

In other embodiments, the featured image-guided radiotherapy method for tumor treatment is applicable to treatment of locally advanced tumor invading the adjacent organs, such as the spinal cord, blood vessels, brachial plexus or other nerve roots, optic chiasm, optic nerves, pituitary, eyes, small and large bowels, trachea, major airways, kidneys, liver, bladder, and genital organs. In some embodiments, the featured image-guided radiotherapy method for tumor treatment is applicable for effective treatment of a tumor larger than 6 centimeter (cm) in diameter.

As an illustration, a locally advanced head and neck cancer may erode into the spinal canal and threaten to produce paralysis through compression of the spinal cord. The current technique allows for shrinkage of the tumor away from the spinal cord because of the high dose gradient inside the tumor while the spinal cord receives a radiation dose that does not exceed the threshold for damage to the spinal cord. A similar technique can be used to spare the eyes and optic nerves from excessive radiation that can produce blindness when the tumor invades into the orbits. Some tumors such as nasopharyngeal cancers have the propensity to invade the brain through the base of skull and compress the cranial nerves and brain producing paralysis of the face, blindness, deafness, and stroke. The current radiotherapy technique allows for decompression of the nerves when the tumor shrink and may potentially save the patient life and/or quality of life because these tumors are inoperable and requires high radiation dose for cure. This new radiotherapy technique can be applied to any tumor site in the body because it kills the tumor from the inside and spares the adjacent radiosensitive organs.

In some embodiments, the featured image-guided radiotherapy method for tumor treatment is applicable to treatment of locally advanced head and neck cancer with serious toxicity during radiation.

Radiation therapy dose is measured in Gray or centigray (cGy) (1 Gray=100 cGy). Most tumors often require a total dose of 7000 cGy delivered over six to seven weeks of treatment for possible local control. However, the total radiation dose is not limited to 7000 cGy delivered over six to seven weeks and can be greater than the aforementioned total dose, for example, the total radiation dose may be at least 7500 cGy. A radiation dose delivered in a day is called fraction and by convention, may be limited to 180-200 cGy per day. In patients with known radio-resistant tumor such as melanoma or renal cancer, radiation dose is increased to 250 cGy or more because of the tumor's ability to repair radiation damage.

In some embodiments, the total energy delivered during one treatment cycle, such as six to seven weeks, with the featured tumor treatment of internal boost is equal to the total energy regulated or specified by the Radiation Therapy Oncology Group (RTOG) with one radiation dose level applied to the planning treatment volume (PTV). In some embodiments, the total energy delivered during one treatment cycle, such as six to seven weeks, with the featured tumor treatment of internal boost is larger than the total energy regulated or specified by the Radiation Therapy Oncology Group (RTOG) with one radiation dose level applied to the planning treatment volume (PTV). With the featured tumor treatment of internal boost, the radiation energy is tuned to focus within internal part of the tumor, rather than distributed uniformly around planning treatment volume, which includes the tumor volume itself and beyond. The total energy is referred as the total radiation energy absorbed for the entire volume where radiation treatment is received.

In some embodiments, the total energy delivered during one treatment cycle, such as six to seven weeks, with the featured tumor treatment of internal boost is equal to the total energy with the traditional radiation treatment method using one radiation dose level applied to the planning treatment volume (PTV). In some embodiments, the total energy delivered during one treatment cycle, such as six to seven weeks, with the featured tumor treatment of internal boost is larger than the total energy with the traditional radiation treatment method using one radiation dose level applied to the planning treatment volume (PTV). With the featured tumor treatment of internal boost, the radiation energy is tuned to focus within internal part of the tumor, rather than distributed uniformly around planning treatment volume, which includes the tumor volume itself and beyond. The total energy is referred as the total radiation energy absorbed for the entire volume where radiation treatment is received.

In some embodiments, the boosted region (120) is more than 20% of the tumor volume within the tumor boundary (115). In other embodiments, the the boosted region (120) is more than 30% of the volume within the tumor boundary (115). In still other embodiments, the boosted region (120) is more than 40% of the volume within the tumor boundary (115). In some embodiments, the boosted region (120) is more than 50% of the volume within the tumor boundary (115). In some embodiments, the boosted region (120) is more than 60% of the volume within the tumor boundary (115). In some embodiments, the boosted region (120) is at least 70% of the volume within the tumor boundary (115). In some embodiments, the boosted region (120) is between 70% and 90% of the volume within the tumor boundary (115). In some embodiments, the boosted region (120) is between 70% and 80% within the tumor boundary (115). In some embodiments, the boosted region (120) is between 80% and 90% within the tumor boundary (115).

In some embodiments, the prescribed radiation dose is between 180 and 200 centiGray (cGy), while the boosted radiation dose is about 250 centiGray (cGy) or above. For example, the boosted radiation dose is at least 300 centiGray (cGy). In some embodiments, the average decreasing rate is about 10% per millimeter.

In some embodiments, the average radiation dose in the safety region (125) is 5% less than the radiation dose in the boosted region (120). In some embodiments, the average radiation dose in the safety region (125) is 10% less than the radiation dose in the boosted region (120). In some embodiments, the average radiation dose in the safety region (125) is 15% less than the radiation dose in the boosted region (120). In some embodiments, the average radiation dose in the safety region (125) is 20% less than the radiation dose in boost region (120). In some embodiments, the average radiation dose in the safety region (125) is 25% less than the radiation dose in the boosted region (120). In some embodiments, the average radiation dose in the safety region (125) is 30% less than the radiation dose in the boosted region (120). In some embodiments, the average radiation dose in the safety region (125) is at least 30% less than the radiation dose in the boost region (120).

In some embodiments, the predetermined distance between the boosted region boundary and tumor boundary is uniform. In some embodiments, the predetermined distance between the boosted region boundary and tumor boundary is non-uniform, i.e. the predetermined distance varies between the boosted region boundary and tumor boundary. The predetermined minimum distance (126) between the boosted region boundary and tumor boundary is dependent on the boosted radiation dose and the prescribed radiation dose. In some embodiments, the predetermined minimum distance (126) is about 1 cm. In some embodiments, the predetermined minimum distance (126) is between 0.05 and 0.1 cm. In some embodiments, the predetermined minimum distance (126) is between 0.1 and 0.25 cm. In some embodiments, the predetermined minimum distance (126) is between 0.25 and 0.5 cm. In some embodiments, the predetermined minimum distance (126) is between 0.5 and 0.75 cm. In some embodiments, the predetermined minimum distance (126) is between 0.75 and 1 cm. In some embodiments, the predetermined minimum distance (126) is between 1 and 2 cm. In some embodiments, the predetermined minimum distance (126) is between 2 and 5 cm.

Similarly, in the case of radiation resistant tumor treatment, the predetermined minimum distance (126) between the boosted region boundary and tumor boundary is dependent on the boosted radiation dose and the prescribed radiation dose. In some embodiments, the boosted radiation dose is between 300-450 centiGray/day or above and the average decreasing rate is 10% per millimeter.

Figure 4:
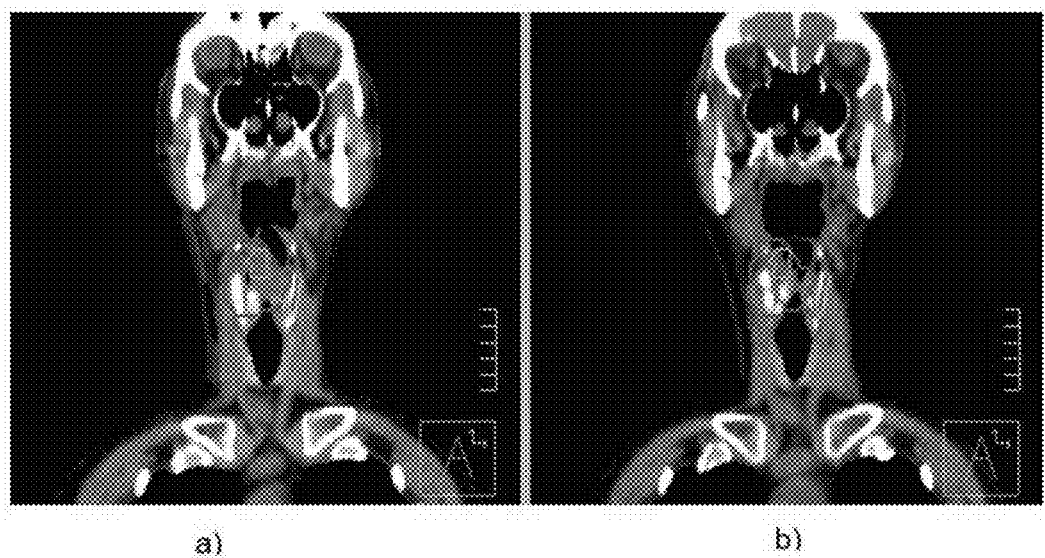
FIG. 4 shows a front view comparison of radiation treatment results of the present method before and after treatment.
Figure 5:
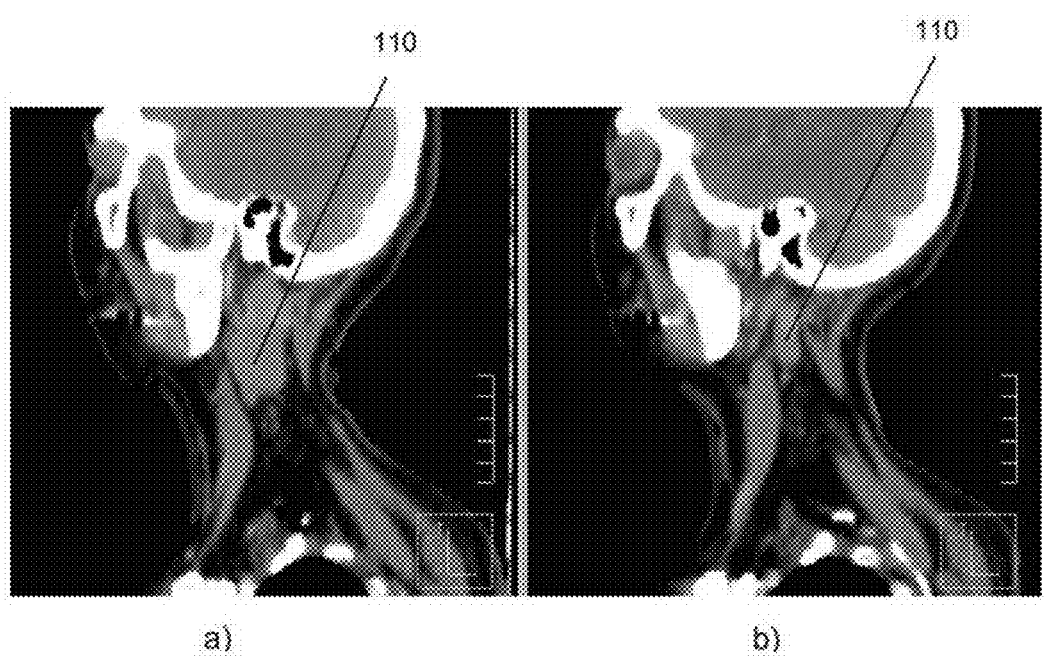
FIG. 5 shows a side view comparison of radiation treatment results before and after treatment.
Figure 6A:
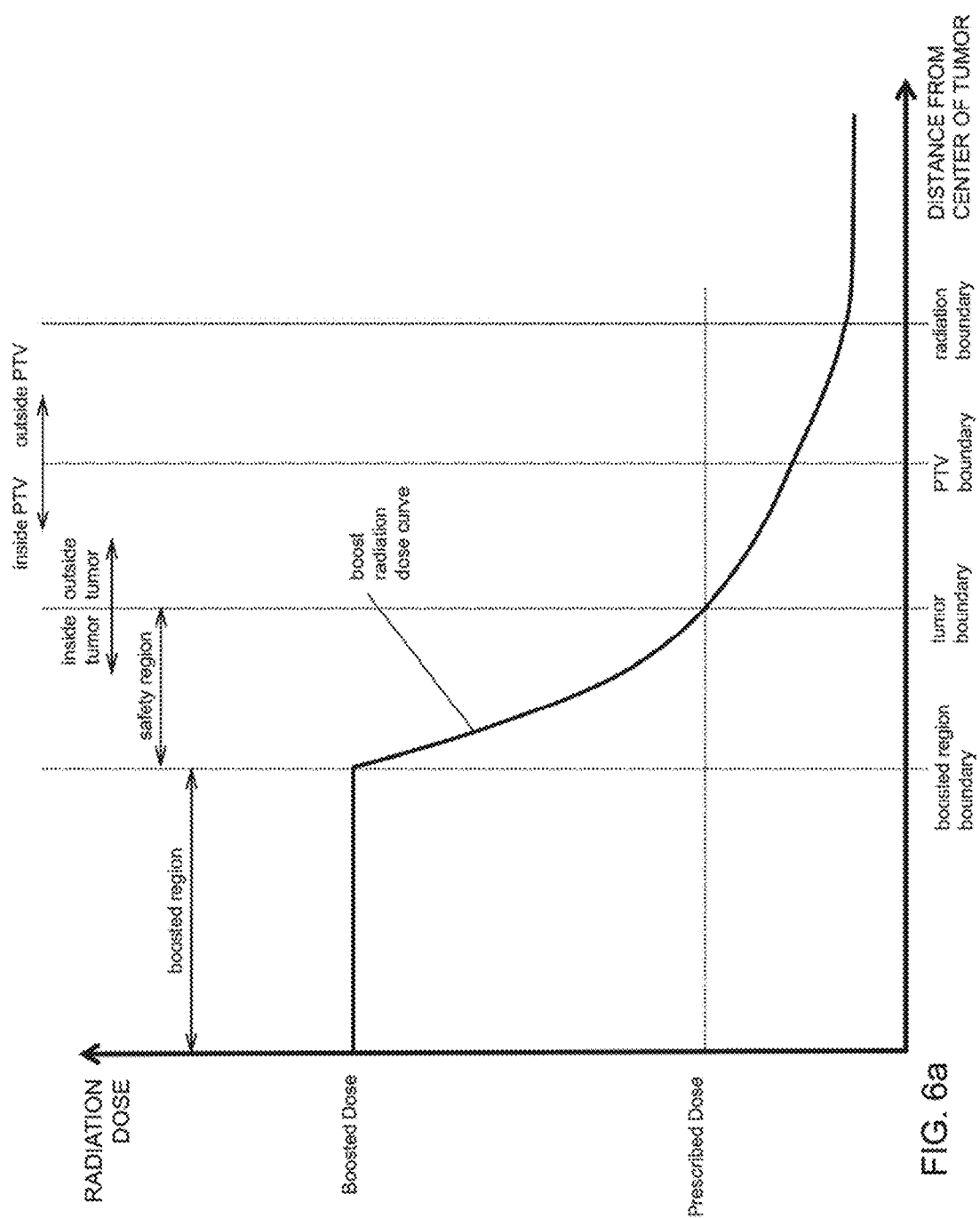
FIGS. 6a and 6b show a radiation dose comparison between the present method and a traditional method.
Figure 6B:
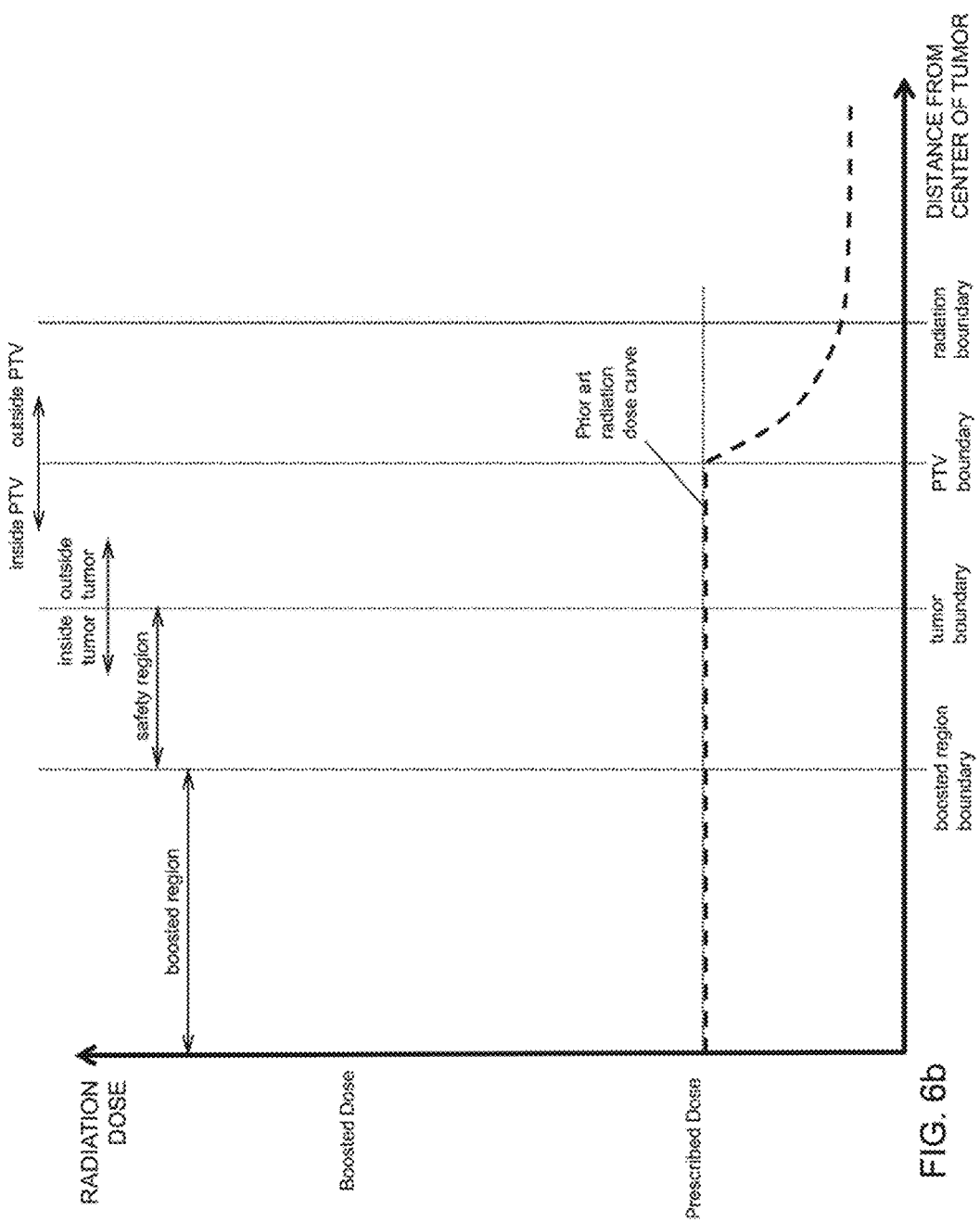
Figure 7:
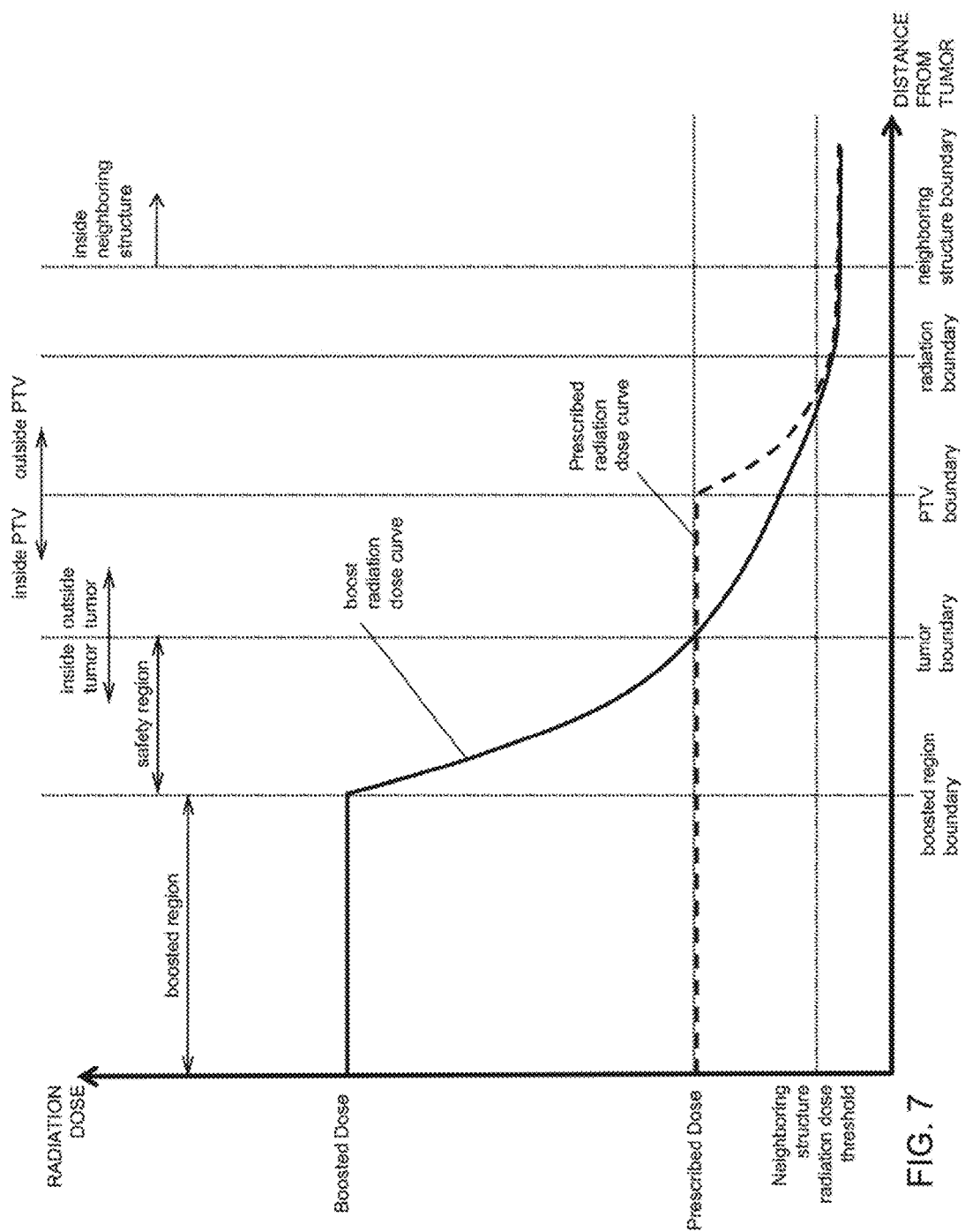
FIG. 7 shows a combined radiation dose comparison of the boosted radiation dose and the prescribed radiation dose. A critical feature of FIG. 7 shows that the radiations doses decrease at a rate such that a radiation dose at the neighboring structure is below a radiation threshold of the neighboring structure.

The experimental comparison of treatment using the present method before and after treatment is shown in FIGS. 4 and 5. FIG. 4a and FIG. 5a show the image before treatment in front and side view respectively. FIG. 4b and FIG. 5b show the image after treatment in front and side view respectively. The redline represents the tumor treated to 200 centigray (cGy) a day. The pink line represents the internal boost treated 220 cGy a day (110%). At least 70% of the tumor received 110%. The tumor shrinks during radiation and now there is air (black) inside the tumor because it melts like snow from the high radiation dose.

Table 1 and Table 2 show some typical radiation dose for typical RTOG Guideline method and the present method. As shown in the tables, the boosted radiation dose ranges from about 220-350 cGy/day for radiation-sensitive tumors and about 300-450 cGy/day for radiation resistant tumors. The boosted radiation dose ranges are not limited to the aforementioned doses and can range significantly higher that these doses.

tumor volume. The treatment is repeated daily. At each new treatment, a new scanning for tumor location and size have been done before applying of radiation treatment to ensure

TABLE 1

Treatment for Radiation Sensitive Tumors

| | RTOG Guideline method | | | Present method | | | |
| --- | --- | --- | --- | --- | --- | --- | --- |
| Tumor | Prescribed radiation dose (cGy/day) | Percentage of PTV1 receiving >110% of prescribed dose | Drop off rate beyond Tumor boundary | Predetermined average Safety Region radiation dose (cGy/day) | Boosted Region radiation dose (cGy/day) | Percentage of Boosted Region receiving >110% of prescribed dose | Drop off rate beyond Tumor boundary |
| Squamous Carcinoma | 180-200 | <20% | 10%/mm | 200-315 | 220-350 | 70%-90% | 10%/mm |
| Adeno Carcinoma | 180-200 | <20% | 10%/mm | 200-315 | 220-350 | 70%-90% | 10%/mm |
| small cell Carcinoma | 180-200 | <20% | 10%/mm | 200-315 | 220-350 | 70%-90% | 10%/mm |
| Lymphoma Carcinoma | 180-200 | <20% | 10%/mm | 200-315 | 220-350 | 70%-90% | 10%/mm |
| Transitional cell Carcinoma | 180-200 | <20% | 10%/mm | 200-315 | 220-350 | 70%-90% | 10%/mm |

(PTV: planning target volume, which is equal to entire tumor region)

TABLE 2

Treatment for Radiation Resistant Tumors

| | RTOG Guideline method | | | Present method | | | |
| --- | --- | --- | --- | --- | --- | --- | --- |
| Tumor | Prescribed radiation dose (cGy/day) | Percentage of PTV receiving >110% of prescribed dose | Drop off rate beyond Tumor boundary | Predetermined average Safety Region radiation dose (cGy/day) | Boosted Region radiation dose (cGy/day) | Percentage of Boosted Region receiving >110% of prescribed dose | Drop off rate beyond Tumor boundary |
| melanoma | 250 | <20% | 10%/mm | 275-400 | 300-450 | 70%-90% | 10%/mm |
| renal cancer | 250 | <20% | 10%/mm | 275-400 | 300-450 | 70%-90% | 10%/mm |

The radiation for use in accordance with the present invention may be delivered using any appropriate beam radiation techniques, for example, Intensity Modulated Radiotherapy (IMRT) and Image-guided radiotherapy (IGRT). With IGRT the clinician can see the pictures of the tumor daily. With IMRT, the clinician cannot see the pictures. Systems which can be used in accordance with the present invention include ones made by Tomotherapy, Varian, Siemens, Elekta, Toshiba and the like. Varian has Varian True Beam, Rapid Arc, Varian EX or IX.

CLINICAL EXAMPLE 1

In this example, a 75-year old white male patient with a stage T4N2M0 laryngeal cancer (locally advanced tumor that spread to the cervical lymph nodes producing enlargement of the lymph node between 3 to 6 cm and without distant metastases) had been treated with a prescribed tumor dose of 7000 cGy at 200 cGy per day and boosted radiation level of 7700 cGy at 220 cGy/day for 35 days. The original tumor was obstructing the airway and threatened to asphyxiate the patient. After 20 days of treatment (or 4000 cGy prescribed tumor dose and 4400 cGy boosted radiation dose for boosted region), the tumor shrunk to 20% of its initial size allowing the patient to breathe. The treatment has no complication observed. Boosted region is about 80% of the tumor volume. The treatment is repeated daily. At each new treatment, a new scanning for tumor location and size have been done before applying of radiation treatment to ensure the accuracy of the dose delivered. The cancer disappeared after treatment both on clinical exams and diagnostic X-rays. The patient has a normal voice following treatment and remains free of cancer 16 months following treatment.

CLINICAL EXAMPLE 2

In this example, a 71-year-old patient with a stage T4N0M0 (locally advanced tumor that did not spread to the cervical lymph nodes and distant organs) oropharyngeal cancer had been treated with a tumor dose of 7000 cGy (200 cGy a day) and boosted radiation level of 7700 cGy at 220 cGy/day for 35 days. The tumor extended upward from the soft palate to the nasopharynx, anteriorly to the hard palate and oral cavity, and downward to the base of tongue preventing patient from swallowing food. After 15 days of treatment (or 3000 cGy prescribed tumor dose treatment and 3300 cGy boosted radiation dose for boosted region), the tumor had reduced to 90% of its initial size allowing the patient to swallow again. The treatment has no complication observed. Boosted region is about 85% of the tumor volume. The treatment is repeated daily. At each new treatment, a new scanning for tumor location and size was performed before applying radiation treatment to verify treatment accuracy. The cancer completely disappeared at the end of radiation treatment. The patient is currently disease free 21 months following treatment and is able to eat and drink normally without any complications.

CLINICAL EXAMPLE 3

In this example, a 56-year-old white male with a stage T4N3M0 oropharyngeal cancer (locally advanced tumor that invaded the cervical lymph nodes producing enlargement of the lymph nodes more than 6 cm and without distant metastases) had been treated with a dose of 7000 cGy (200 cGy/day) to the tumor and bilateral lymph nodes and boosted radiation level of 7700 cGy (220 cGy/day for 35 days. Original neck nodes measured 8 cm in diameter. After 20 days of treatment (or 4000 cGy prescribed tumor radiation dose and 4400 cGy boosted radiation dose for boosted region), the neck nodes had reduced to a diameter about 3 cm. The treatment has no complication observed. Boosted region is about 70% of the tumor volume and neck nodes. The treatment is repeated each day. At each new treatment, a new scanning for tumor location and size was performed before applying radiation treatment to verify treatment accuracy. The tumor and neck nodes completely disappeared following treatment and the patient is cancer-free five months after treatment without any complications.

As used herein, the term "about" refers to plus or minus 10% of the referenced number. For example, an embodiment wherein a radiation dose is about 250 centiGray (cGy) includes radiation dose between 225 and 275 centiGray (cGy).

The disclosures of the following U.S. patents are incorporated in their entirety by reference herein: U.S. Publication No. 2007/0014454, U.S. Publication No. 2006/0067469, and U.S. Publication No. 2011/0075806.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. An image-guided radiotherapy method for treating a radio-resistant tumor, wherein the method comprises:
   a. obtaining a three-dimensional visualized tumor image to identify the tumor;
   b. identifying a tumor boundary of the tumor;
   c. identifying a planning target volume (PTV) region outside of the tumor boundary, wherein the PTV region is between the tumor boundary and a planning target volume boundary;
   d. identifying a boost region within the tumor boundary, wherein a predetermined safety region is between the boost region and the tumor boundary, wherein the predetermined safety region has a predetermined minimum distance from a boost region boundary to the tumor boundary, wherein the boost region is more than 20% of a tumor volume within the tumor boundary;
   e. identifying a neighboring structure adjacent to the tumor, wherein the neighboring structure is bounded within a neighboring structure boundary;
   f. applying a boosted radiation dose in the boost region;
   g. simultaneously applying with the boosted radiation dose a predetermined prescribed radiation dose in the PTV region and within the tumor boundary, wherein the predetermined prescribed radiation dose is smaller than the boosted radiation dose; and
   h. repeating steps a. through g. for each subsequent treatment;
   wherein the boosted radiation dose is at least 110% of the predetermined prescribed radiation dose for the tumor, wherein the predetermined prescribed radiation dose is about 250 centiGray per day and the boosted radiation dose ranges from about 300 to 450 centiGray per day;
   wherein the radiation resistant tumor includes melanoma or renal cancer;
   wherein the predetermined minimum distance is dependent on one or more of the boosted radiation dose, the prescribed radiation dose, an importance level, and a radiation sensitivity level of the neighboring structure;
   wherein the boosted radiation dose outside of the boost region decreases at a boost dose decreasing rate such that the boosted radiation dose at the tumor boundary is equal to the predetermined prescribed radiation dose; and
   wherein the boosted radiation dose and the predetermined prescribed radiation dose decrease at an average decreasing rate such that the boosted radiation dose and the predetermined prescribed radiation dose at the neighboring structure boundary are below a radiation dose threshold of the neighboring structure.

* * * * *